United States Patent [19]

Ladd

[11] 3,933,850

[45] Jan. 20, 1976

[54] METHOD FOR MAKING N,N'-METHYLENE BISMALEIMIDES AND PRODUCTS MADE THEREFROM

[75] Inventor: John R. Ladd, Ballston Lake, N.Y.

[73] Assignee: General Electric Company, Schenectady, N.Y.

[22] Filed: May 28, 1974

[21] Appl. No.: 473,429

Related U.S. Application Data

[62] Division of Ser. No. 246,287, April 21, 1972, Pat. No. 3,833,609.

[52] U.S. Cl. ............................................. 260/326.26
[51] Int. Cl.$^2$ ........................................ C07D 207/44
[58] Field of Search ............................... 260/326.26

[56] References Cited

UNITED STATES PATENTS 2,971,944 2/1961 Chow et al. ............... 260/326.26 X

*Primary Examiner*—Raymond V. Rush
*Attorney, Agent, or Firm*—William A. Teoli; Joseph T. Cohen; Jerome C. Squillaro

[57] ABSTRACT

A method is provided for making a variety of N,N'-methylene bismaleimides by introducing boron trifluoride into a maleimide mixture containing either paraformaldehyde or methanol maleimide. The N,N'-methylene bismaleimides made by the subject method can be symmetrical or unsymmetrical and are useful for making polyimides.

3 Claims, No Drawings

METHOD FOR MAKING N,N'-METHYLENE BISMALEIMIDES AND PRODUCTS MADE THEREFROM

This is a division, of application Ser. No. 246,287, filed Apr. 21, 1972 now U.S. Pat. No. 3,833,609.

The present invention relates to a method for making N,N'-methylene bismaleimides and products made therefrom. More particularly, the present invention relates to the use of a boron trifluoride as a catalyst in a maleimide mixture of paraformaldehyde or a N-methanol maleimide.

The maleimides provided by the present invention are selected from the class consisting of symmetrical N,N'-methylene bismaleimides of the formula,

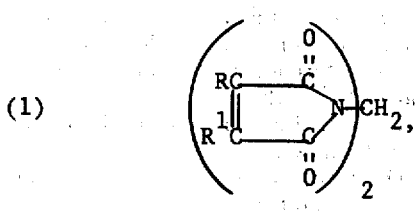

and unsymmetrical N,N'-methylene bismaleimides,

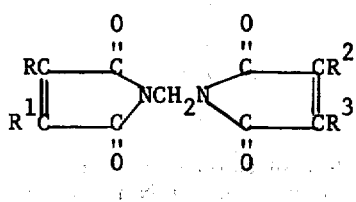

where R, $R^1$, $R^2$ and $R^3$ are the same or different monovalent radicals selected from the class consisting of hydrogen, monovalent hydrocarbon radicals, and halogen radicals.

Radicals included by R-$R^3$ are for example, hydrogen, aryl radicals, such as tolyl, xylyl, naphthyl, etc.; alkyl radicals such as methyl, ethyl, propyl, butyl, pentyl, hexyl, etc.; cycloaliphatic radicals such as, cyclobutyl, cyclopentyl, cyclohexyl, cycloheptyl, etc.; halogen radicals, such as bromo, chloro, iodo, fluoro, etc.

There is also provided by the present invention, a method which comprises, (1) passing boron trifluoride into a maleimide mixture selected from, a. a mixture of formaldehyde, and about two moles, per mole of formaldehyde of a maleimide of the formula,

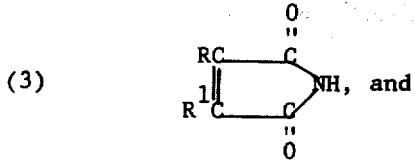

b. a mixture of substantially equal moles of said maleimide of (a) and an N-methanolmaleimide of the formula,

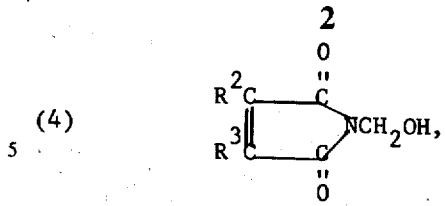

and (2) recovering an N,N'-methylene bismaleimide from the mixture of (1), where R, $R^1$, $R^2$ and $R^3$ are as previously defined.

Included by the symmetrical bismaleimides of formula 1 are for example, N,N'-methylenebisdichloromaleimide, N,N'-methylenebiscitraconimide, N,N'-methylbenebischloromaleimide. There are included by the unsymmetrical bismaleimides of formula 2, N-(citraconimidomethyl)maleimide, N-(maleimidomethyl)chloromaleimide, N-(citraconimidomethyl) dichloromaleimide.

In the practice of the invention, the symmetrical bismaleimides of formula 1 can be prepared by initially dissolving maleimide in an organic solvent, such as for example, methylene chloride, chloroform, etc., and adding paraformaldehyde to the resulting solution in an effective amount. An effective amount of paraformaldehyde is any amount which is at least sufficient to provide one half mole of formaldehyde, per mole of maleimide. Boron trifluoride is then introduced into the mixture at a rate which does not allow for any excess to escape from the reaction mixture. As soon as the mixture is saturated with boron trifluoride, excess solvent can be decanted from the mixture, followed by the addition of a solvent, such as methanol to effect the precipitation of product. Recovery of the product and its purification can be effected by standard techniques, such as by filtration, recrystallization in boiling aliphatic alcohol, etc.

Alternatively, if it is desired to make unsymmetrical methylene bismaleimide, boron trifluoride can be introduced into an organic solvent solution of substantially equal molar amounts of the maleimide and the methanol maleimide. The precipitation and the recovery of the resulting methylene bismaleimide can then proceed in accordance with the previously described procedure.

During the introduction of the boron trifluoride to the above described mixture, stirring or agitation by other known means can be employed to facilitate the interaction of the various ingredients of the mixture. Temperatures in the range of between 0°C to 60°C can be employed. It has been found that an exothermic reaction results upon the introduction of boron trifluoride, which can require the use of an external cooling means, such as an ice bath.

It has been found that the final product is generally a crystalline material, which has a relatively sharp melting point. However, in instances where unsymmetrical methylene bismaleimides are made, a mixture of up to 3 methylene bismaleimides can occur, which may interfere with the recovery of a pure compound. Resolution of the mixture can be facilitated by the use of such analytical means as chromotography, etc.

The methylene bismaleimides of the present invention can be employed in combination with other reagents, such as arylene diamines or polyalkylene diamines to make a variety of polyimides, such as shown by Kovacic U.S. Pat. No. 2,818,405 and Grundschober et al. U.S. Pat. No. 3,380,964 and Sambeth et al. U.S. Pat. No. 3,406,148 etc.

In order that those skilled in the art will be better able to practice the invention, the following examples are given by way of illustration and not by way of limitation. All parts are by weight.

EXAMPLE 1

Boron trifluoride was introduced into a mixture of 9.71 parts of maleimide, 12.7 parts of N-methanol maleimide and about 500 parts of methylene chloride, while the resulting mixture was stirred. The mixture became exothermic and an ice bath was applied to maintain the temperature of the mixture below about 30°C. Boron trifluoride was introduced at a rate so little or no excess escaped from the reaction mixture. There was obtained a gummy precipitate. The methylene chloride was then decanted from the mixture and there was added to the resulting product, about 100 parts of methanol with cooling. There was obtained 15 parts of a white solid. It was recrystallized from about 250 parts of boiling aqueous ethyl alcohol to produce a crystalline product having a faint yellow color and a melting point of 171°C. Based on method of preparation the product was N,N'-bismaleimide.

When equal molar amounts of N,N'-methylenebismaleimide and methylene dianiline heated together as a 10 percent solution in dimethylformamide at 150°–155° for three hours, a powdered resin was formed which was precipitated by addition of the reaction mixture in methyl alcohol. Upon fusing the powdered resin at 350°C, it was found to form a film having good dielectric properties.

EXAMPLE 2

Boron trifluoride was passed into a mixture of 19.4 parts of maleimide, and 3 parts of paraformaldehyde dissolved in about 500 parts of methylene chloride. When the mixture was saturated with boron trifluoride, as shown by the tendency for it to escape from the surface, there was obtained a gummy precipitate following the procedure of Example 1. Fifteen parts of a crystalline product was obtained from the mixture having about the same melting point. Based on method of preparation, the product was N,N'-methylene bismaleimide.

EXAMPLE 3

Boron trifluoride was slowly passed into a mixture of 0.2 parts of citraconimide and 0.03 parts of paraformaldehyde dissolved in about 5 parts of methylene chloride. After the mixture had been saturated with boron trifluoride, the methylene chloride was decanted yielding a gummy product. The gummy product was recrystallized from methanol and a crystalline material was obtained. Based on method of preparation, the crystalline product was N,N'-methylene biscitraconimide having the formula,

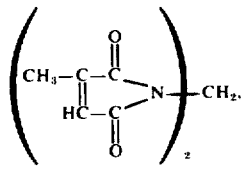

A mixture of about 25 parts of polyisoprene diamine, 0.176 parts of diethylene triamine and about 4 parts of N,N'-methylene biscitraconimide is milled and cast into a thin film. The film is cured at about 150°C for 15 minutes. An elastomer is obtained exhibiting valuable insulating properties.

EXAMPLE 4

Boron trifluoride was slowly introduced into a mixture of 0.13 part of N-methanol maleimide and 0.11 part of citraconimide in about 5 parts of methylene chloride. Following the procedure of Example 3, there was obtained a crude crystalline material. Based on method of preparation, the product was N(N'-maleimidomethyl)citraconimide.

Although the above examples are limited to only a few of the very many N,N'-methylene bismaleimides which can be made in the practice of the present invention, it should be understood that the present invention is directed to a much broader class of both symmetrical N,N'-bismaleimides of formula 1, and unsymmetrical N,N'-bismaleimides of formula 2.

What I claim as new and desire to secure by Letter Patent of the United States is:

1. A method which comprises, (1) saturating with boron trifluoride at temperature of from 0°C to 60°C a maleimide mixture selected from
   a. a mixture of formaldehyde, an organic solvent and about two moles, per mole of formaldehyde of a maleimide of the formula,

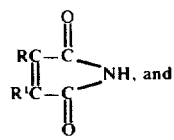

b. A mixture of substantially equal moles of said maleimide of (a) and an N-methanolmaleimide of the formula,

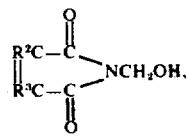

in the presence of an organic solvent, and
2. recovering an N,N'-methylene bismaleimide from the mixture of (1), where R, R$^1$, R$^2$ and R$^3$ are the same or different monovalent radicals selected from the class consisting of hydrogen, methyl, ethyl, propyl, butyl, pentyl, hexyl, cyclobutyl, cyclopentyl, cyclohexyl, cycloheptyl, and halogen.

2. A method in accordance with claim 1, where there is employed maleimide mixture (a).

3. A method in accordance with claim 1, where there is employed maleimide mixture (b).

* * * * *